(12) United States Patent
Noone et al.

(10) Patent No.: US 6,228,073 B1
(45) Date of Patent: May 8, 2001

(54) ANGIOGRAPHY LUER HUB HAVING WINGS PROXIMAL TO THE PLURALITY OF GRIPS AND STRAIN RELIEF

(75) Inventors: Michael S. Noone, Londonderry, NH (US); Cheryl Fay-Lauria, Burlingtion; Bruce Adams, Malden, both of MA (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/211,821

(22) Filed: Dec. 15, 1998

(51) Int. Cl.[7] .................................................. A61M 25/00
(52) U.S. Cl. ..................... 604/533; 604/525; 604/177; 604/905; 128/912
(58) Field of Search .................. 604/164, 171, 604/177, 264, 523, 525, 533, 534, 905; 128/DIG. 26, DIG. 6, 912, 164.01, 174

(56) References Cited

U.S. PATENT DOCUMENTS

| | | |
|---|---|---|
| 3,721,231 | 3/1973 | Hubert . |
| 4,013,080 | 3/1977 | Froning . |
| 4,194,504 | 3/1980 | Harms et al. . |
| 4,326,519 * | 4/1982 | D'Alo et al. . |
| 4,389,210 | 6/1983 | Genese . |
| 4,445,893 | 5/1984 | Bodicky . |
| 4,682,981 | 7/1987 | Suzuki et al. . |
| 4,840,613 | 6/1989 | Balbierz . |
| 4,875,481 | 10/1989 | Higgins . |
| 5,021,049 | 6/1991 | Howard . |
| 5,167,647 | 12/1992 | Wijkamp et al. . |
| 5,284,476 | 2/1994 | Koch . |
| 5,330,449 | 7/1994 | Prichard et al. . |
| 5,380,301 | 1/1995 | Prichard et al. . |
| 5,466,230 * | 11/1995 | DAvila ............................... 604/256 |
| 5,512,052 | 4/1996 | Jesch . |
| 5,599,325 * | 2/1997 | Ju et al. .............................. 604/282 |
| 5,651,776 | 7/1997 | Appling et al. . |
| 5,725,513 | 3/1998 | Ju et al. .............................. 604/280 |
| 5,989,223 * | 11/1999 | Chu et al. ........................... 604/167 |
| 5,993,399 * | 11/1999 | Pruitt et al. ........................ 600/562 |
| 6,068,622 * | 5/2000 | Sater et al. ......................... 604/524 |

FOREIGN PATENT DOCUMENTS

| | | |
|---|---|---|
| 0 168289 | 1/1986 | (EP) . |
| 0 366336 | 5/1990 | (EP) . |
| 0 554841 | 8/1993 | (EP) . |

OTHER PUBLICATIONS

Mar. 1994 USCI Product Catalog and Price List, p. 5–22.
Two photographs (one color and one black and white) of SciMed Maxxum Manifold; the date and origination of this reference is unknown. The existence of this reference prior to the application filing date of Dec. 15, 1998, is acknowledged. A prototype will be furnished upon request.

(List continued on next page.)

*Primary Examiner*—Richard K. Seidel
*Assistant Examiner*—L. Thanh
(74) *Attorney, Agent, or Firm*—Sterne, Kessler, Goldstein & Fox, P.L.L.C.

(57) ABSTRACT

A hub for connecting a medical catheter in fluid communication with a medical device, such as a syringe, includes a tubular shaped body member which has an outer surface that is formed with a plurality of grips. The hub also has a pair or diametrically opposed wings which extend from the outer surface of the body member and it has a proximal end which is formed as a female luer fitting for engagement with the medical device. The distal end of the hub is formed with a spiral strain relief element having a passageway which receives the proximal end of the medical catheter. In operation, the spiral relief element supports the medical catheter and prevents kinking of the catheter near the hub during flexure of the catheter by providing for a progressive transition from the relative rigidity of the hub to the flexure required by the catheter.

15 Claims, 2 Drawing Sheets

OTHER PUBLICATIONS

Photograph Of SciMed ST 55 CM Guiding Catheter (806 E01777);. The existence of this reference prior to the application filing date of Dec. 15, 1998, is acknowledged. A prototype will be furnished upon request.

Marketing literature for the SciMed Maxxum, PTCA Dilation Catheter, Instructions for Use, 6 pages, (8½×11) dated Aug., 1996.

* cited by examiner

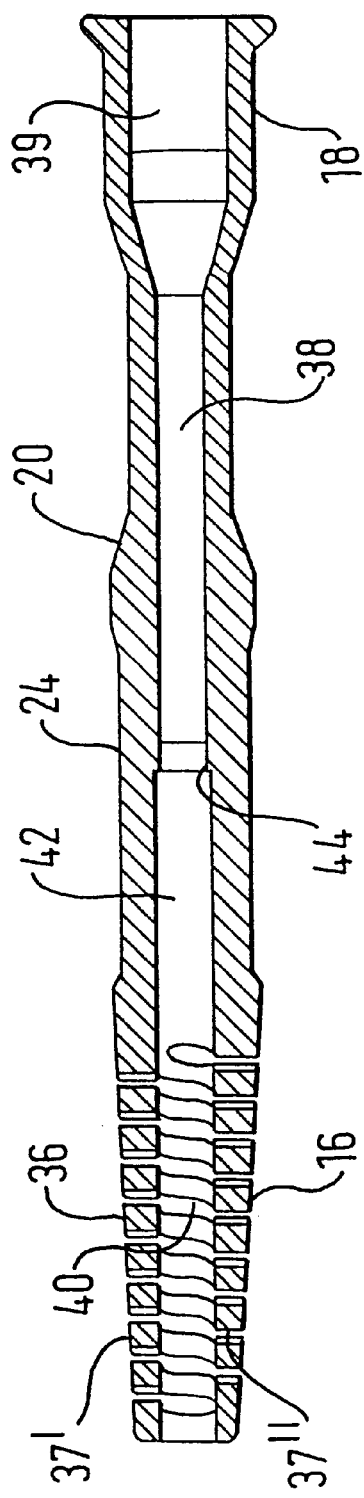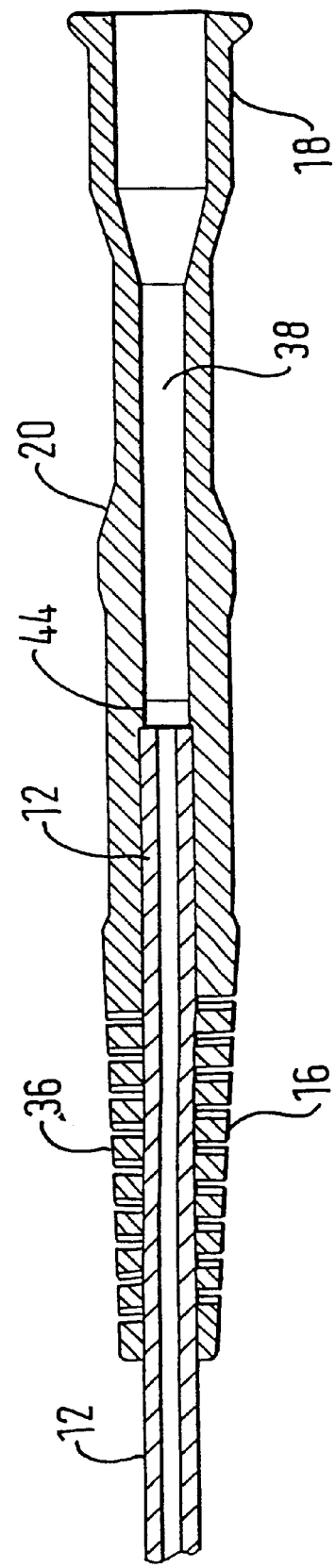
FIG. 3A
FIG. 3B

ANGIOGRAPHY LUER HUB HAVING WINGS PROXIMAL TO THE PLURALITY OF GRIPS AND STRAIN RELIEF

FIELD OF THE INVENTION

The present invention pertains generally to connector hubs for medical catheters. More particularly, the present invention pertains to connector hubs which are used to establish fluid communication between an interventional medical catheter and an extracorporeal medical device. The present invention is particularly, but not exclusively, useful for providing tactile control for a physician during the positioning and use of the medical catheter during a clinical procedure.

BACKGROUND OF THE INVENTION

The general purpose of a luer hub is to connect a catheter to some mating piece of equipment such as a syringe, a power injection tube or a manifold. It happens, however, that the luer hub is also used by physicians to control the positioning of the catheter as it is being advanced into the vasculature of a patient. In order for the physician to properly control the catheter during such an advancement, it is necessary to subject the catheter to both axial and rotational forces. A major concern in all of this is that, while the forces which are exerted on the catheter must provide for the desired degree of catheter flexibility and operational control, they can not be allowed to cause the catheter to kink or otherwise become inoperative.

Various types of connecting hubs have been proposed for specialized uses with various types of catheters. For example, U.S. Pat. No. 4,445,893, which issued to Bodicky for an invention entitled "Infusion Apparatus," discloses an intravenous catheter placement device which includes a hub that is attached directly to a rigid cannula. In another example, U.S. Pat. No. 4,875,481, which issued to Higgins for an invention entitled "Catheter with Coiled Wire Attachment," discloses a wire having a coiled proximal end that is positioned in a hub, and an elongated distal end which extends from the hub through the PTCA catheter. The wire in this case is used for steering control over the catheter by rotation of the hub. In yet another example, U.S. Pat. No. 5,167,647, which issued to Wijkamp et al. for an invention entitled "Catheter with a Strain Relief Member," discloses a tubular shaped strain relief member which extends distally from the hub and over a short portion of the catheter. None of these examples, however, teach or suggest a hub and strain relief element which are formed, in combination, as an integral unit, and which provide for a progressive transition from the relative rigidity of the hub to the flexure required by the associated catheter. More recently, however, efforts have been made to address this issue. For example, U.S. application Ser. No. 09/021,682, and U.S. application Ser. No. 09/046,241, which are each assigned to the same assignee as the present invention, both disclose spiral strain relief elements which are designed to provide such a transition, albeit with different structure than disclosed herein for the present invention.

An angiographic catheter, due to the nature of its specific function, can be designed to have a relatively small diameter. Hence, in comparison with infusion catheters, such as PTCA catheters and atherectomy catheters which often require relatively large diameters, the angiographic catheter and other small diameter catheters are particularly susceptible to kinking. It often happens that this problem is most pronounced near the hub where control forces are imparted by the physician to control movement of the catheter into a patients vasculature.

In light of the above, it is an object of the present invention to provide a connector hub which provides the physician with control and sensitivity during the placement of a catheter into the vasculature of a patient. It is another object of the present invention to provide a connector hub for a catheter which will provide for a progressive transition from the relative rigidity of the hub to the flexure required by the catheter. Yet another object of the present invention is to provide a connector hub for a catheter which presents the hub and a strain relief element as an integral unit. Another object of the present invention is to provide a connector hub for a catheter which is ergonomically efficient in providing a physician with control structure for rotating and advancing the catheter into the vasculature of a patient. Still another object of the present invention is to provide a connector hub for a catheter which is easy to manufacture, relatively simple to use and comparatively cost effective.

SUMMARY OF THE PREFERRED EMBODIMENTS

A luer connecting hub for interconnecting a catheter in fluid communication with a piece of medical equipment includes a substantially tubular shaped body member which is formed with a bore that extends longitudinally through the body member. The outer surface of the body member is formed with a plurality of longitudinally oriented grips, and proximal to the grips there are a pair of diametrically opposed wings, or lobes, which extend outwardly from the body member. The proximal end of the body member is formed as a female luer fitting for engaging a medical device, such as a syringe or a manifold, in fluid communication with the bore of the body member.

Extending from the distal end of the connecting hub is an integral strain relief element which is formed as an articulated spiral having a plurality of segmented turns. More specifically, the spiral shaped strain relief element establishes a passageway for receiving a catheter tube therethrough. Thus, when the proximal end of the catheter tube is connected to the distal end of the bore, through the body member of the hub, the spiral shaped strain relief element will surround and support a proximal portion of the catheter tube.

With this combination of structure, the spiral strain relief element is able to bend in a controlled manner to provide a progressive transition from the relative stiffness imposed by the hub on the catheter tube to the full flexure capability of the catheter tube. Importantly, this progressive transition avoids unwanted and undesirable kinking in the proximal portion of the catheter tube near the luer hub.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3A is a cross sectional view of the connector hub as seen along the line 3—3 in FIG. 2; and FIG. 3B is a cross sectional view of the connector hub as seen in FIG. 3A with a catheter tube attached to the connector hub.

DESCRIPTION OF THE PREFERRED EMBODIMENT

Figure 1:
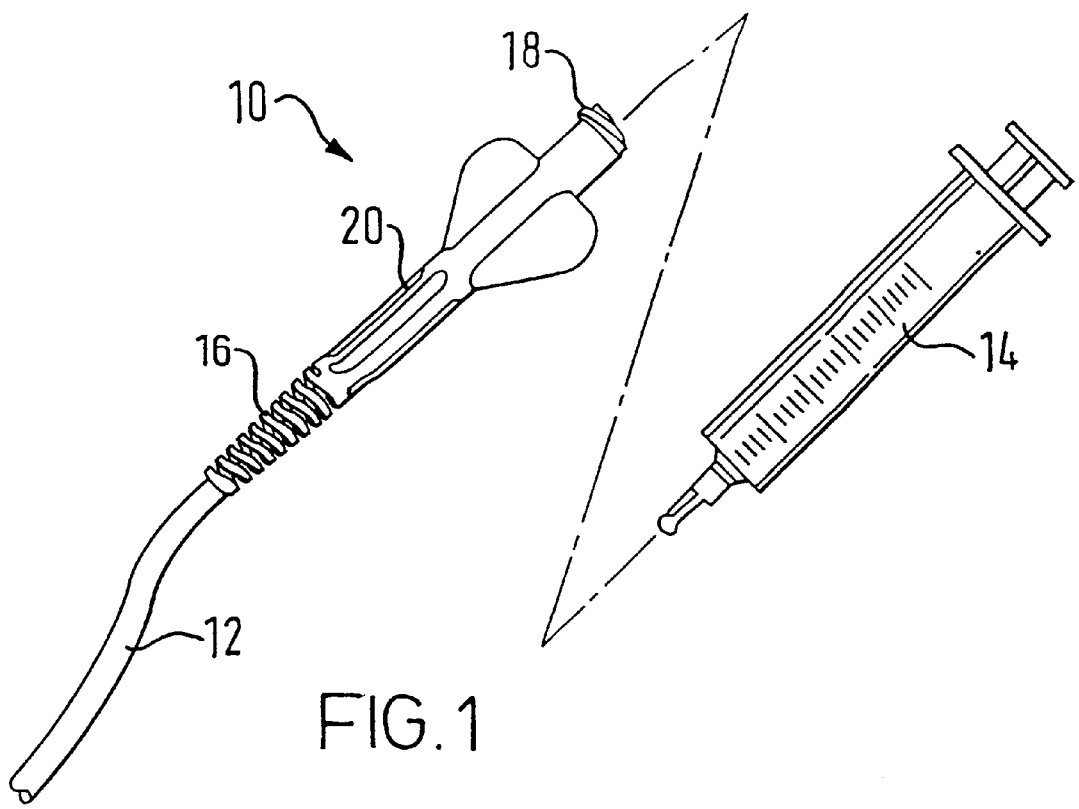
FIG. 1 is a perspective view of the connector hub of the present invention shown connected with a catheter tube and positioned for engagement with a medical device.

Referring initially to FIG. 1, a luer connector hub in accordance with the present invention is shown in its operational environment and generally designated 10. As intended for the hub 10 of the present invention, it is to be used to interconnect a catheter tube 12 (shown attached to the distal end of the hub 10) in fluid communication with a medical device 14 (shown positioned for attachment to the proximal end of the hub 10). More specifically, the catheter tube 12 of particular interest for the present invention is one that is suitable for use as an angiography catheter or a guide catheter. Consequently, the catheter tube 12 will be fairly flexible and have a relatively small diameter. Specifically, the catheter tube 12 will typically be made of a plastic material, such as polyurethane, and will have an outside diameter which will be in the range of from four to seven french (4–7F). Not so specifically, the medical device 14 can be of any type well known in the pertinent art. For instance, the medical device 14 can include equipment such as the syringe (shown in FIG. 1), power injection tubes (not shown) or manifolds (not shown).

In FIG. 1 it will be seen that the luer connector hub 10 of the present invention is an integral unit which includes three interconnected elements. These elements are: a spiral strain relief element 16 at the distal end of the hub 10, a female luer fitting 18 at the proximal end of the hub 10, and a body member 20 which is intermediate the spiral strain relief element 16 and luer fitting 18. The specific external features of the connector hub 10 can, perhaps, best be seen with reference to FIG. 2.

Figure 2:
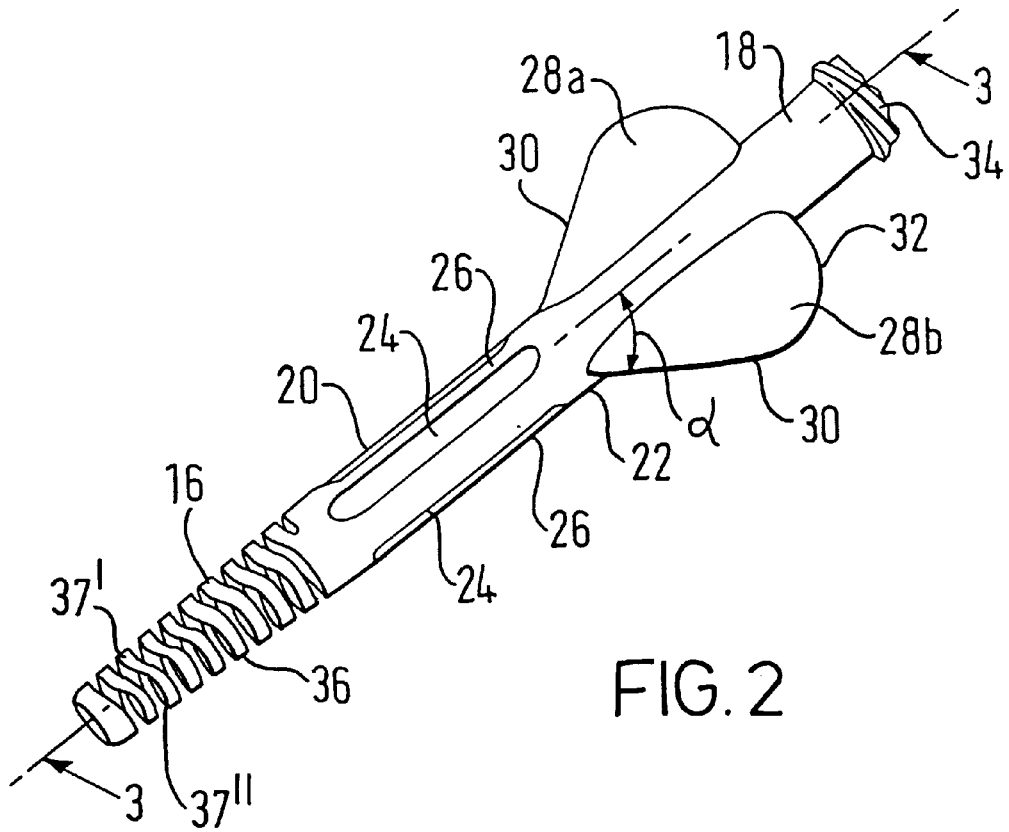
FIG. 2 is a perspective view of the connector hub.

FIG. 2 shows that the outer surface 22 of the connector hub 10 is formed with a plurality of grips which are manifest as longitudinally oriented parallel depressions 24. Between these depressions 24 are an equal number of longitudinally oriented parallel ridges 26. Collectively these depressions 24 and ridges 26 combine to create flutes which provide a slip resistant surface that can be used by the physician to rotate the hub 10, and accordingly, the catheter tube 12. The longitudinal length of the depressions 24 and ridges 26 are generally a matter of design choice and can be selected to give the physician the best tactile sensitivity. Further, and perhaps more importantly, the length of the depressions 24 and ridges 26 (flutes) are sufficient to allow a physician to effectively rotate the hub 10 between a thumb and forefinger.

FIG. 2 also shows that the outer surface 22 of the body member 20 of luer connector hub 10 is formed with a pair of diametrically opposed wings 28a and 28b. As shown, each of the wings 28a,b has a leading edge 30 which is generally straight and inclined with the longitudinal axis of the luer connector hub 10 through an angle α. For the present invention, the angle α will be in the range of 25° to 45°, and will preferably be about 35°. Each of the wings 28a,b also has a generally arcuate trailing edge 32 which is convex and which transitions between the outer surface 22 of body member 20 and the leading edge 30. With this geometry, the wings 28a,b present a heart-shaped structure which can be used by the physician to control the angular position of the hub 10 and the torsional forces that are applied to the catheter tube 12. The exact dimensions of the wings 28a,b are somewhat a matter of design choice, but should be chosen to give the physician optimal control.

Still referring to FIG. 2, it will be seen that additional external features of the luer connector hub 10 of the present invention include a thread 34 which is formed onto the luer fitting 18. The purpose of thread 34 is facilitate a fluid tight connection between the luer connector hub 10 and the medical device 14. Additionally, it is seen in FIG. 2 that the spiral strain relief element 16 comprises a plurality of longitudinally spaced turns 36. These turns 36 are integrally contiguous and, together, create a generally helix shaped structure which forms the spiral strain relief element 16. More specifically, as perhaps best appreciated by cross referencing FIG. 2 and FIG. 3A, each of the turns 36 in strain relief element 16 is segmented and includes both a primary segment 37' and a secondary segment 37". As shown, the primary segments 37' are axially off-set from the secondary segments 37" and are generally oriented in planes that are perpendicular to the longitudinal axis of the hub 10. As also shown, along the strain relief element 16 the primary segment 37' of one turn 36 is directly interconnected with the secondary segment 37" of an adjacent turn 36, and vice versa, i.e. the secondary segment 37" of one turn 36 is directly interconnected with the primary segment 37' of an adjacent turn 36. This specific structure for the strain relief element 16 is particularly well suited for manufacture by injection molding. For purposes of the present invention, the spiral strain relief element 16 will contain between nine and twenty turns 36 per inch. The internal structural features of the luer connector hub 10 of the present invention are, perhaps, best seen in FIG. 3A.

In FIG. 3A it will be seen that the body member 20 of luer connector hub 10 is formed with a bore 38 which extends longitudinally along the entire length of the body member 20. Further, it will be seen that luer fitting 18 is 30 formed with a fluid channel 39 which is in fluid communication with the bore 38. Additionally, it will be seen that the turns 36 of spiral strain relief element 16 form a passageway 40, and that there is a cavity 42 formed at the distal end of the body member 20 which is in fluid communication with the bore 38. It is to be appreciated that the entire connector hub 10 can be manufactured as an integral unit by any means well known in the pertinent art, such as injection molding.

In the assembly of luer connector hub 10 of the present invention with the catheter tube 12, as best seen in FIG. 3B, the proximal end of the catheter tube 12 is inserted through the passageway 40 of spiral strain relief element 16, and into the cavity 42 of body member 20. Insertion of the catheter tube 12 continues until the catheter tube 12 abuts the shoulder 44. With the catheter tube 12 in position on the luer connector hub 10 as shown in FIG. 3B, the catheter tube 12 is bonded to the connector hub 10 in any manner well known in the pertinent art, such as by heat bonding or adhesive bonding. Importantly, the turns 36 of spiral strain relief element 16 are not bonded to the catheter tube 12. With this cooperation of structure, the spiral strain relief element 16 is able to bend with the catheter tube 12 and provide a progressive transition for bending of the catheter tube 12 as it extends distally from the luer connector hub 10. Further, the medical device 14 can be engaged with the fitting 18 of hub 10 and the hub 10 will then be operational.

While the particular Angiography Luer Hub as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A connector hub attached in fluid communication with a medical catheter which comprises:
   a substantially tubular shaped body member having a proximal end and a distal end and defining a longitudinal axis, said body member being formed with a bore extending longitudinally therethrough and having an outer surface formed with a plurality of grips;
   a pair of diametrically opposed planar wings mounted on said body member, wherein said wings are substantially displaced along said longitudinal axis from said plurality of grips;
   a fitting formed with a fluid channel, said fitting extending from said proximal end of said body element to join said fluid channel in fluid communication with said bore; and
   a strain relief element formed with a plurality of segmented turns, said strain relief element extending from said distal end of said body member, wherein said medical catheter is in fluid communication with said distal end of said body member.

2. A hub as recited in claim 1 wherein said strain relief element includes between nine and twenty turns per inch, and wherein each turn includes a primary segment and a secondary segment with said secondary segment axially offset from said primary segment, and wherein said turns are interconnected with each other by attachment of a primary segment of one turn to a secondary segment of another turn.

3. A hub as recited in claim 1 wherein said strain relief element forms a passageway for receiving a portion of said medical catheter therein.

4. A hub as recited in claim 1 wherein said fitting is a female luer connector.

5. A hub as recited in claim 1 wherein said grips are a plurality of depressions formed into said outer surface of said body member.

6. A hub as recited in claim 1 wherein said grips are a plurality of ridges formed into said outer surface of said body member.

7. A hub as recited in claim 1 wherein each said wing has a distal leading edge and a proximal trailing edge with said leading edge being oriented at an angle to said axis to widen said wing in a distal to proximal direction and said trailing edge being a convex curve to transition between said body member and said leading edge.

8. A medical catheter system engageable in fluid communications with a medical device, said catheter system comprising:
   a substantially tubular medical catheter formed with a lumen and having a proximal end and a distal end; and
   an elongated connector hub unit having a distal end formed for connection in fluid communication with said medical catheter and a proximal end formed for connection in fluid communication with said medical device, said hub unit being formed with a bore extending longitudinally therethrough for fluid communication between said distal end and said proximal end, said hub unit having an outer surface formed with a plurality of grips and formed with a pair of planar wings extending outwardly from said outer surface, said hub unit being further formed with a strain relief element formed with a plurality of segmented turns, wherein each turn includes a primary segment and a secondary segment with said secondary segment axially offset from said primary segment, and wherein said turns are interconnected with each other by attachment of said primary segment of one turn to said secondary segment of another turn, said strain relief element extending, distally from said distal end of said hub unit.

9. A system as recited in claim 8 wherein said grips are a plurality of depressions formed into said outer surface of said body member.

10. A system as recited in claim 8 wherein said grips are a plurality of ridges formed into said outer surface of said body member.

11. A system as recited in claim 8 wherein said spiral shaped strain relief element includes between nine and twenty turns per inch.

12. A system as recited in claim 8 wherein each said wing has a distal leading edge and a proximal trailing edge with said leading edge being oriented at an angle to said axis to widen said wing in a distal to proximal direction and said trailing edge being a convex curve to transition between said body portion and said leading edge.

13. An integrally molded catheter hub comprising:
   a tubular body having a proximal end, a distal end, an outer surface, and a bore extending longitudinally therethrough;
   a female catheter fitting forming the proximal end of the body;
   a pair of diametrically opposed planar wings formed on the body at a location distal of said fitting;
   a strain relief forming the distal end of the body, the strain relief having a plurality of longitudinally spaced turns that taper distally; and
   a slip resistant surface formed on the outer surface of the body at a location distal of said wings.

14. A catheter hub according to claim 13 wherein said slip resistant surface comprises a plurality of grips.

15. A catheter hub according to claim 13 wherein said longitudinally spaced turns are segmented turns, each turn including a primary segment and a secondary segment with the secondary segment axially offset from the primary segment, and wherein said turns are interconnected with each other by attachment of the primary segment of one turn to the secondary segment of another turn.

* * * * *